United States Patent [19]
Shionoya et al.

[11] Patent Number: 5,356,757
[45] Date of Patent: Oct. 18, 1994

[54] IMMOBILIZED ENZYME FILM, PROTEIN IMMOBILIZED FILM AND PROCESS FOR FORMING THE SAME

[75] Inventors: Kiseko Shionoya; Atsushi Saito, both of Tokyo, Japan

[73] Assignee: NEC Corporation, Tokyo, Japan

[21] Appl. No.: 972,560

[22] Filed: Nov. 6, 1992

[30] Foreign Application Priority Data

Nov. 8, 1991 [JP] Japan ................. 3-319711
Jan. 17, 1992 [JP] Japan ................. 4-025944

[51] Int. Cl.$^5$ ............................. G03C 5/00
[52] U.S. Cl. ..................... 430/315; 435/288
[58] Field of Search ................ 430/315; 435/288

[56] References Cited

U.S. PATENT DOCUMENTS 4,795,707 1/1989 Niiyama et al. ............. 435/288
4,894,339 1/1990 Hanazato et al. ............ 435/288

*Primary Examiner*—John Kight, III
*Assistant Examiner*—T. Mosley
*Attorney, Agent, or Firm*—Burns, Doane, Swecker & Mathis

[57] ABSTRACT

Disclosed are an immobilized enzyme film, characterized in that said film is formed using an enzyme solution prepared by adding 1 to 3 parts by weight of a 50 to 100 wt % water-soluble crosslinking agent having at least two epoxy groups in the molecule and 1 to 3 parts by weight of a 1 to 2 wt % glutaraldehyde to 1 to 3 parts by weight of a 10 to 50 wt % aqueous protein solution containing an enzyme, and a process for forming the same on an ion-sensitive field effect transistor. The thus formed immobilized enzyme film is of an uniform thickness and stable by virtue of its increased hydrophilicity and higher elasticity, whereby deactivation of the enzyme to be caused by the shrinkage of the film can be prevented.

11 Claims, 6 Drawing Sheets

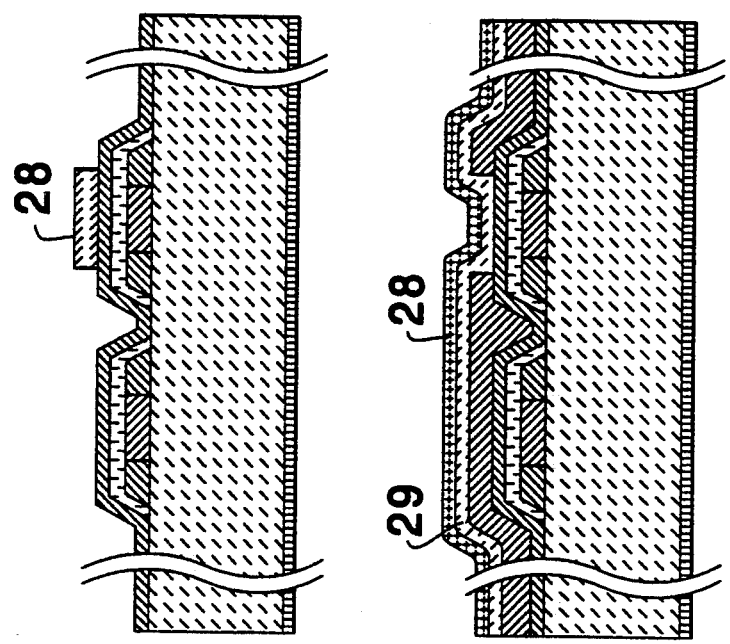
Fig. 5d
Fig. 5e
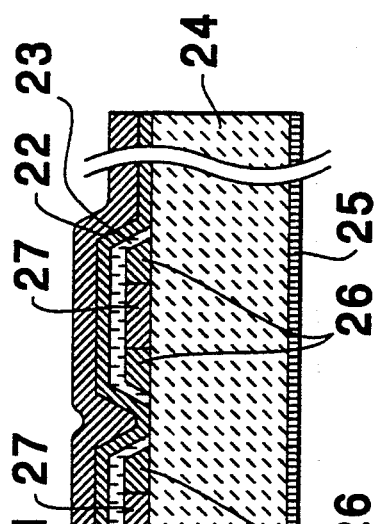
Fig. 5a
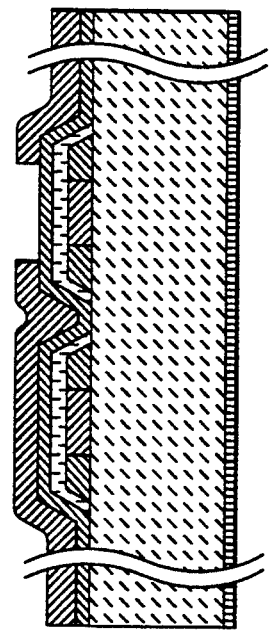
Fig. 5b
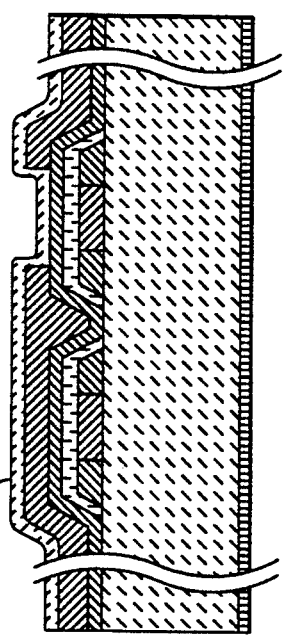
Fig. 5c

IMMOBILIZED ENZYME FILM, PROTEIN IMMOBILIZED FILM AND PROCESS FOR FORMING THE SAME

BACKGROUND OF THE INVENTION

1. Field of the Invention

The present invention relates to an immobilized enzyme film, a protein immobilized film and a process for forming the same, particularly to an immobilized enzyme film for biosensors and a process for forming the same. More specifically, the present invention relates to a process for forming an immobilized enzyme film or a protein immobilized film in an integrated semiconductor biosensor having such film formed on the surface of an ion-sensitive field effect transistor.

2. Description of the Prior Art

Attempts have so far been made to utilize enzymes in the field of analysis. Particularly, biosensors employing an immobilized enzyme film and various kinds of electrochemical devices are speedy, convenient and highly sensitive analytical means. Recently, a biosensor comprising a micro-electrochemical device fabricated using the silicon IC production technology and an enzyme film formed on the surface thereof has been proposed (Japanese Utility Model Publication No. 61-50262 (Japanese Utility Model Application No. 59-134995)).

As one example of such enzyme film formed on the sensitive section of such microsensor, a film formed using a mixture of an enzyme, a protein and glutaraldehyde has been used. According to this method, an immobilized enzyme film is obtained using a mixture prepared by adding glutaraldehyde to a protein solution containing an enzyme.

There is so far known a semiconductor biosensor for determining concentration of a specific organic substance contained in a solution comprising an ion-sensitive field effect transistor (hereinafter abbreviated as ISFET) having an enzyme immobilized on the surface thereof. This ISFET biosensor determines at the ISFET the concentration of a specific organic substance by detecting a change in the hydrogen ion concentration in the solution which occurs when the specific organic substance undergoes a chemical reaction by the catalytic action of the enzyme. As such immobilized enzyme film having selectivity, urease immobilized films for urea detection and glucose oxidase immobilized film for glucose detection are known.

A process for producing such biosensor has been proposed by Kuriyama, Nakamoto et al., in which glutaraldehyde is used as a crosslinking agent for an albumin immobilized film or an immobilized enzyme film to pattern a glutaraldehyde-albumin crosslinked film and a glutaraldehyde-albumin-enzyme film on a wafer by photolithography (Japanese Patent Application Nos. 59-209165 and 60-194333). Meanwhile, Miyamoto proposed a method in which such film is formed by spin coating with cooling so as to obtain a film having a uniform thickness (Japanese Patent Application No. 63-325216).

As described above, when an immobilized enzyme film is formed according to the prior art technique, the resulting film assumes hydrophobicity since the film is crosslinked by glutaraldehyde, so that the water content after drying will be extremely low to increase internal strain of the film and give stress to the enzyme retained in the film, in turn, accelerating deactivation of the enzyme, disadvantageously.

On the other hand, in the case of a glutaraldehyde-crosslinked enzyme film having no protective film such as of saccharide, a conformational shift occurs in the enzyme due to the shrinkage of the film during film formation or determination, inevitably causing deactivation of the enzyme. Besides, the crosslinking reaction to be effected by the glutaraldehyde must be controlled by cooling so as to obtain a film having a uniform thickness.

SUMMARY OF THE INVENTION

The present invention is directed to overcome the prior art problems and to provide a stable immobilized enzyme film or a protein immobilized film having increased hydrophilicity and elasticity so as to prevent deactivation of the enzyme.

According to a first aspect of the present invention, there is provided an immobilized enzyme film, characterized in that the film is formed using an enzyme solution prepared by adding 1 to 3 parts by weight of a 50 to 100 wt % water-soluble crosslinking agent having at least two epoxy groups in the molecule and 1 to 3 parts by weight of a 1 to 2 wt % glutaraldehyde to 1 to 3 parts by weight of a 10 to 50 wt % aqueous protein solution containing an enzyme.

According to a second aspect of the present invention, there is provided a process for forming an immobilized enzyme film, which comprises:

a step of mixing 1 to 3 parts by weight of a 10 to 50 wt % aqueous protein solution containing an enzyme with 1 to 3 parts by weight of a 50 to 100 wt % water-soluble crosslinking agent having at least two epoxy groups in the molecule, followed by vigorous stirring of the resulting mixture with ice cooling;

a step of adding 1 to 3 parts by weight of a 1 to 2 wt % glutaraldehyde to the resulting mixture with continuous ice cooling, followed by vigorous stirring; and a step of applying the resulting mixture by spin coating to a wafer treated with a silane coupling agent.

According to a third aspect of the present invention, there is provided a process for forming an immobilized enzyme film, which comprises:

(a) a step of applying a photoresist soluble in an organic solvent onto a semiconductor wafer on which an ion-sensitive field effect transistor has been formed, followed by removal of the photoresist at a predetermined portion on the surface of the ion-sensitive field effect transistor where an immobilized enzyme film is to be formed;

(b) a step of applying a silane coupling agent by spin coating to treat the predetermined portion on the surface of the ion-sensitive field effect transistor with the silane coupling agent;

(c) a step of applying an aqueous protein solution containing an enzyme and a crosslinking agent onto the thus treated surface of the semiconductor wafer by spin coating; and (d) a step of treating the resulting semiconductor wafer with an organic solvent in which the photoresist is soluble to dissolve the photoresist and lift off the immobilized enzyme film present on the portions other than the predetermined portion on the surface of the ion-sensitive field effect transistor;

wherein the above spin coating step is repeated at predetermined intervals necessary for the crosslinking agent to complete the crosslinking reaction, whereby to form an immobilized enzyme film having a desired thickness at the predetermined portion on the surface of the ion-sensitive field effect transistor; the aqueous protein solution containing an enzyme and a crosslinking agent consisting at least of 1 to 4 parts by weight of a solution containing 1 to 20 % by weight of an enzyme and 10 to 50 % by weight of a protein, 1 to 2 parts by weight of a solution containing 50 to 100 % by weight of a water-soluble crosslinking agent having at least two epoxy groups in the molecule and 1 to 2 parts by weight of a solution containing 1 to 2 % by weight of glutaraldehyde. In the above process, a water-soluble crosslinking agent having at least two epoxy groups in the molecule is preferably applied by spin coating onto the semiconductor wafer, subsequent to the step of treating the predetermined portion on the surface of the ion-sensitive field effect transistor with a silane coupling agent.

According to a fourth aspect of the present invention, there is provided a process for forming a protein immobilized film, which comprises:

(a) a step of applying a photoresist soluble in an organic solvent onto a semiconductor wafer on which an ion-sensitive field effect transistor has been formed, followed by removal of the photoresist at a predetermined portion on the surface of the ion-sensitive field effect transistor where a protein immobilized film is to be formed;

(b) a step of applying a silane coupling agent by spin coating to treat the predetermined portion on the surface of the ion-sensitive field effect transistor with the silane coupling agent;

(c) a step of applying an aqueous protein solution containing a crosslinking agent onto the thus treated surface of the semiconductor wafer by spin coating; and (d) a step of treating the resulting semiconductor wafer with an organic solvent in which the photoresist is soluble to dissolve the photoresist and lift off the protein immobilized film present on the portions other than the predetermined portion on the surface of the ion-sensitive field effect transistor;

wherein the above spin coating step is repeated at predetermined intervals necessary for the crosslinking agent to complete the crosslinking reaction, whereby to form a protein immobilized film having a desired thickness at the predetermined portion on the surface of the ion-sensitive field effect transistor; the aqueous protein solution containing an enzyme and a crosslinking agent being a solution consisting at least of 1 to 4 parts by weight of a solution containing 10 to 50 % by weight of an aqueous protein solution, 1 to 2 parts by weight of a solution containing 50 to 100 % by weight of a water-soluble crosslinking agent having at least two epoxy groups in the molecule and 1 to 2 parts by weight of a solution containing 1 to 2 % by weight of glutaraldehyde. In the above process, a water-soluble crosslinking agent having at least two epoxy groups in the molecule is applied by spin coating onto the semiconductor wafer, subsequent to the step of treating the predetermined portion on the surface of the ion-sensitive field effect transistor with a silane coupling agent.

The aqueous protein solution to be used according to the first or second aspect of this invention may contain a catalyst. The catalyst can be exemplified by trimethylamine, hexamethyltetramine, etc.

The water-soluble crosslinking agent is desirably ethylene polyethylene glycol diglycidyl ether.

According to the first or second aspect of this invention, a hydrophilic and flexible immobilized enzyme film can be obtained, whereby deactivation of the enzyme can be prevented.

In the processes for forming an immobilized enzyme film or a protein immobilized film according to the third or fourth aspect of this invention, the water-soluble crosslinking agent is preferably ethylene polyethylene glycol diglycidyl ether, while the silane coupling agent is preferably triethoxyvinylsilane, ethoxydimethylvinylsilane allyltriethoxysilane or 3-aminopropylethoxysilane.

Meanwhile, according to the third or fourth aspect of this invention, a photoresist soluble in an organic solvent is applied onto a semiconductor wafer and then removed by photolithography at a predetermined portion on the surface of the ISFET where a protein immobilized film or an immobilized enzyme film is to be formed, followed by application of a silane coupling agent by spin coating. The silane coupling agent prevents the protein immobilized film or the immobilized enzyme film to be formed later from coming off the surface of the ISFET.

Subsequent to the above step, a mixture of albumin-glutaraldehyde-water-soluble crosslinking agent having at least two epoxy groups in the molecule or a mixture of enzyme-albumin-glutaraldehyde-water-soluble crosslinking agent having at least two epoxy groups in the molecule is applied by spin coating at room temperature. By virtue of this step, a semiconductor biosensor can be fabricated using a comparatively weak enzyme which is susceptible to deactivation such as urease and practically utilized.

Further, by treating the thus treated semiconductor wafer with an organic solvent in which the photoresist is soluble, the photoresist dissolves in the organic solvent to lift off the protein immobilized film or immobilized enzyme film formed thereon, and thus the protein immobilized film or immobilized enzyme film remains on the surface of the ISFET only. The thus formed protein immobilized film or immobilized enzyme film has a uniform thickness with no fins at the ends of the film.

Moreover, the step of applying a water-soluble crosslinking agent having at least two epoxy groups in the molecule by spin coating, subsequent to the treatment with the silane coupling agent, can further prevent coming off of the protein immobilized film or immobilized enzyme film from the wafer.

BRIEF DESCRIPTION OF THE DRAWINGS

The features of this invention that are believed to be novel are set for with particularity in the appended claims. The invention, together with the objects and advantages thereof, may best be understood by reference to the following description of preferred embodiments taken in conjunction with the accompanying drawings in which:

FIGS. 5(a) to 5(e) show in cross section a flow diagram of fabricating a semiconductor biosensor by the lift-off method;

DETAILED DESCRIPTION OF PREFERRED EMBODIMENTS

Preferred embodiments of the present invention will now be described below referring to the attached drawings.

EXAMPLE 1

Figure 1:
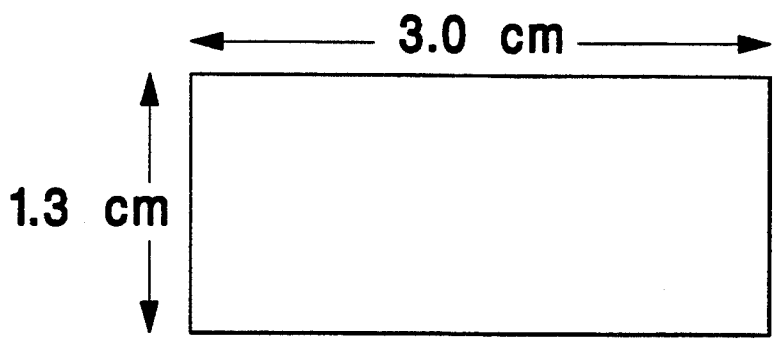
FIG. 1 shows a plan view of a quartz plate employed according to one embodiment of the present invention.
Figure 2:
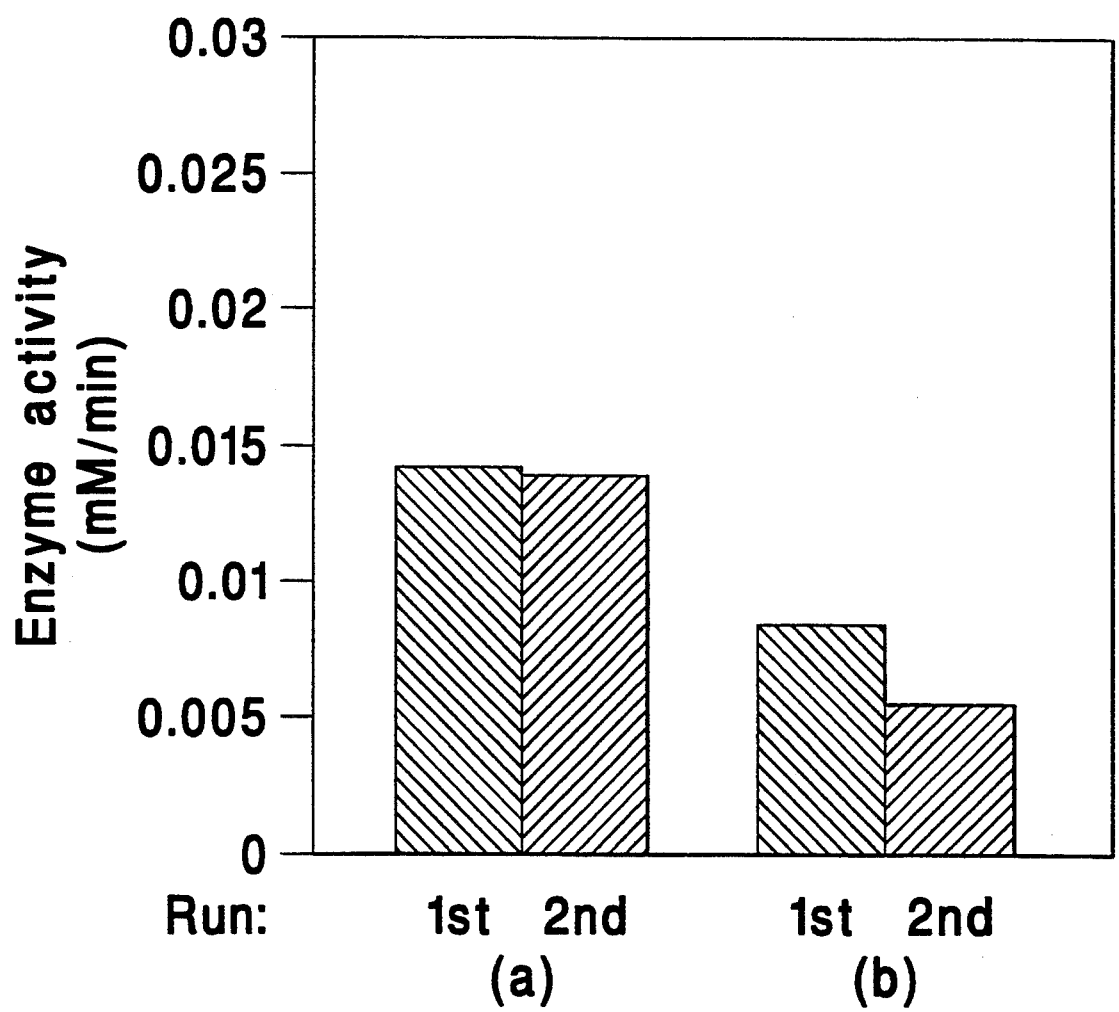
FIG. 2 is a graph showing the enzyme activity of a urease film formed according to one embodiment of the present invention in comparison with that or a prior art urease film.

Onto a quartz plate having dimensions of 1.3 cm×3.0 cm, shown in FIG. 1, a silane coupling agent 3-aminopropyltriethoxysilane was first dropped and then dried by nitrogen gas blowing. Subsequently, 4% by weight of urease was dissolved in 2 parts by weight of a 30 wt % aqueous protein solution, and trimethylamine was quantitatively added thereto as a catalyst, followed by addition of 1 part by weight of a 100 wt % ethylene polyethylene glycol diglycidyl ether with ice cooling. After the resulting mixture was stirred, 1 part by weight of 2 wt % glutaraldehyde was added to the mixture with continuous ice cooling, and the mixture was stirred vigorously to provide an enzyme solution. The thus obtained solution was dropped onto the quartz wafer and spread with a spatula to form a thin film. After the thus formed film was dried well, urease activity of the film was determined by using an absorptiometer. As shown in (a) of FIG. 2, the film exhibited a stable urease activity. Besides, since the film has a higher hydrophilicity over the conventional film, it can hardly be dried and has high elasticity. These are properties unattainable in the prior art immobilized enzyme film ((b) in FIG. 2) formed by using glutaraldehyde only as the crosslinking agent.

EXAMPLE 2

Figure 3A:
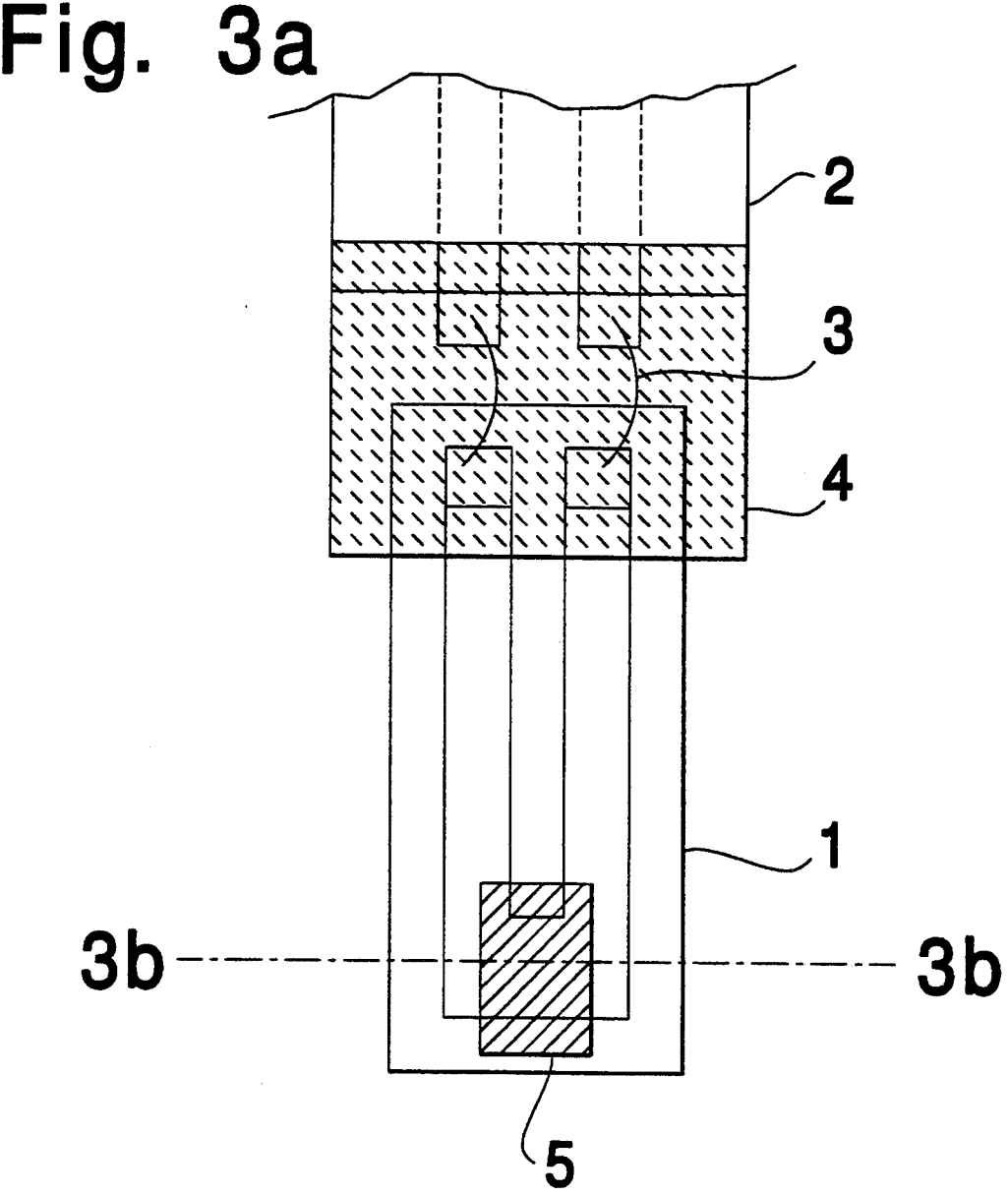
FIG. 3 shows in plan view (a) and cross-sectional view (b) an enzyme electrode according to one embodiment of the present invention.
Figure 3B:
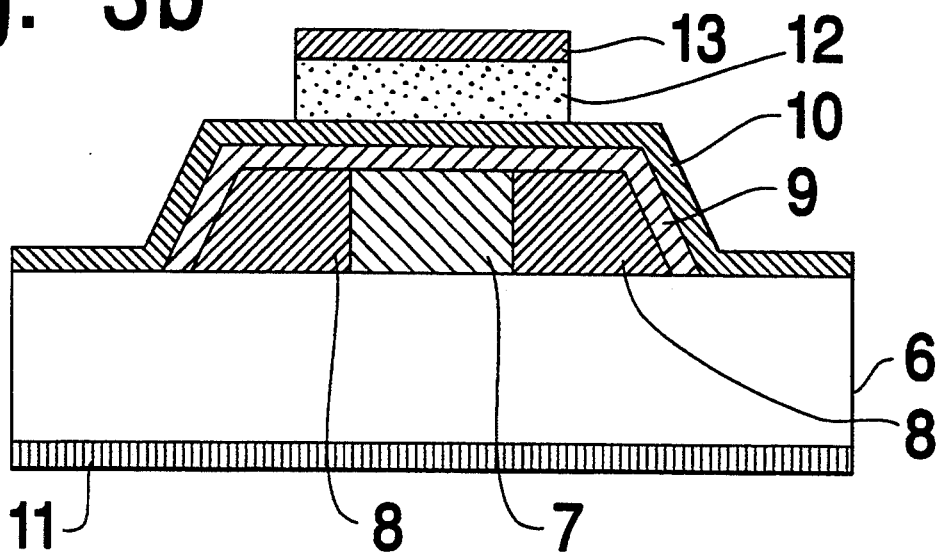
Figure 4:
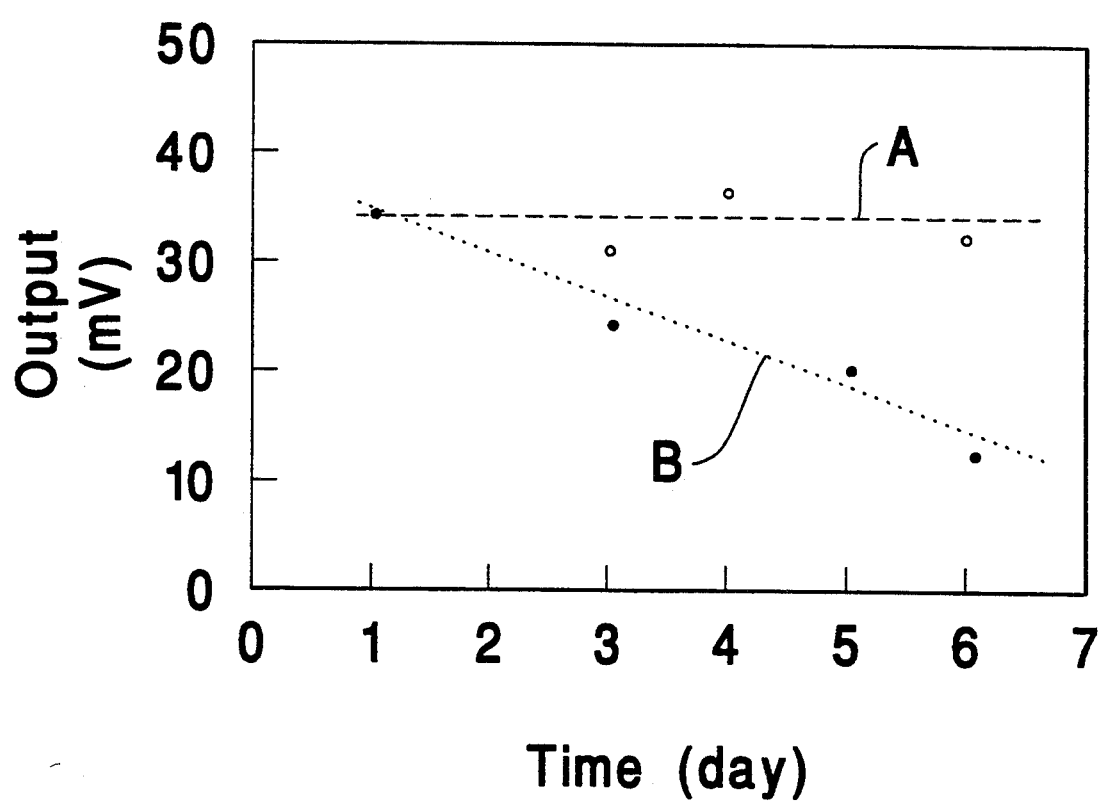
FIG. 4 is a response characteristic curve of a sensor employing the immobilized enzyme film according to the present invention.

In 2 parts by weight of a 30 wt % aqueous protein solution was dissolved 4% by weight of urease, and a catalytic amount of trimethylamine was first added thereto as the catalyst. To the resulting mixture was added 1 part by weight of 100 wt % ethylene polyethylene glycol diglycidyl ether with ice cooling, and then 1 part by weight of 2 wt % glutaraldehyde was added thereto with continuous ice cooling, followed by vigorous stirring to provide an enzyme solution. FIG. 3 shows the structure of an enzyme electrode so as to illustrate the present embodiment of the invention, in which (a) shows a plan view of a biosensor employing an ISFET; and (b) a cross section taken along the line A—A' of (a). In FIG. 3, the reference number 1 denotes an ISFET and 13 an albumin film. In the cross-sectional view (b), the portion of the gate oxide film 9 covered with a silicon nitride film 10 is the hydrogen ion sensitive section. A silane coupling agent 3-aminopropyltriethoxysilane was first dropped to the ion-sensitive section to form a film thereon using a spinner. Next, the above enzyme solution was dropped to the same portion to form an immobilized enzyme film 12 thereon using a spinner. After the immobilized enzyme film 12 was dried well, a mixture prepared by mixing 1 part by weight of a 30 wt % aqueous albumin solution containing no enzyme and 1 part by weight of a 2 wt % glutaraldehyde with ice cooling was dropped onto the immobilized enzyme film 12 to form a film thereon using a spinner. The thus obtained urea sensor has higher hydrophilicity over the conventional urea sensor and gave a stable sensor response with no deactivation of the urease, as shown by the curve A in FIG. 4. On the other hand, the urea sensor employing a conventional glutaraldehyde-crosslinked immobilized enzyme film gave a gradually diminishing response output with time as shown by the curve B.

EXAMPLE 3

As shown in cross-sectional views in the flow diagram of FIGS. 5(a) to 5(d), an organic solvent-soluble photoresist 21 was applied onto a semiconductor wafer having formed there-on an ISFET (see FIG. 5(a)), followed by a step of removing the photoresist at a predetermined portion on the surface of the ISFET where an immobilized enzyme film was to be formed by photolithography (see FIG. 5(b)), a step of applying a silane coupling agent to treat the predetermined portion on the surface of the ISFET with the silane coupling agent, a step of applying by spin coating a mixture prepared by adding 1 part by weight of a 100 wt % water-soluble crosslinking agent having at least two epoxy groups in the molecule to 2 parts by weight of a 30 wt % aqueous albumin solution containing 4 % by weight of an enzyme, and then adding 1 part by weight of 2 wt % glutaraldehyde thereto to form an immobilized enzyme film 28 (see FIG. 5(c)), and a step of treating the thus treated semiconductor wafer with the organic solvent in which the photoresist is soluble to dissolve the photoresist and lift off the immobilized enzyme film present at the portions other than the predetermined portion on the surface of the ISFET; wherein the step of applying the mixture by spin coating was repeated at predetermined intervals necessary for the crosslinking agent to complete the crosslinking reaction, whereby to form an immobilized enzyme film having a desired thickness at the predetermined portion on the surface of the ISFET.

Figure 6A:
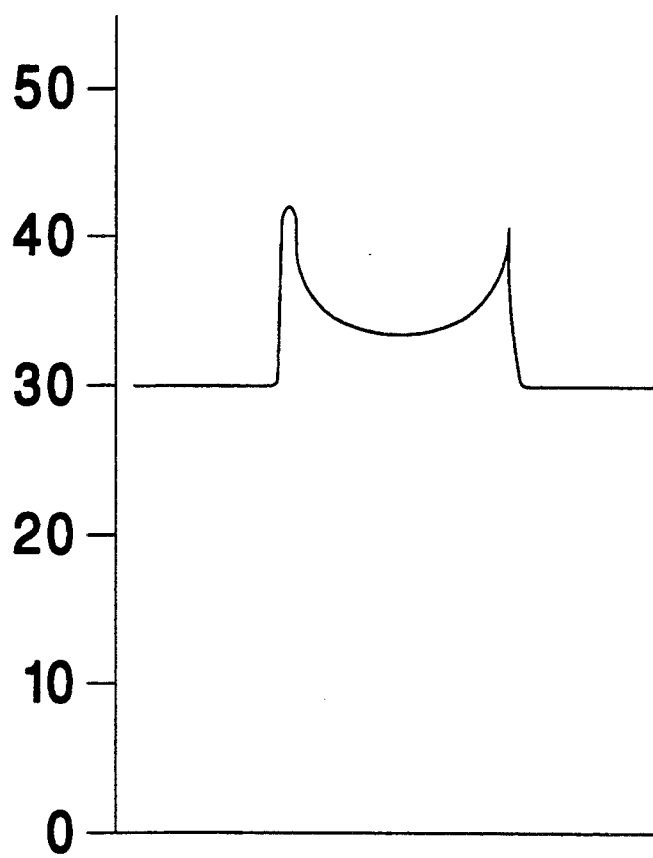
FIGS. 6(a) and 6(b) each show a graph illustrating the thickness of the protein immobilized film or immobilized enzyme film measured by means of a Talystep style device.
Figure 6B:
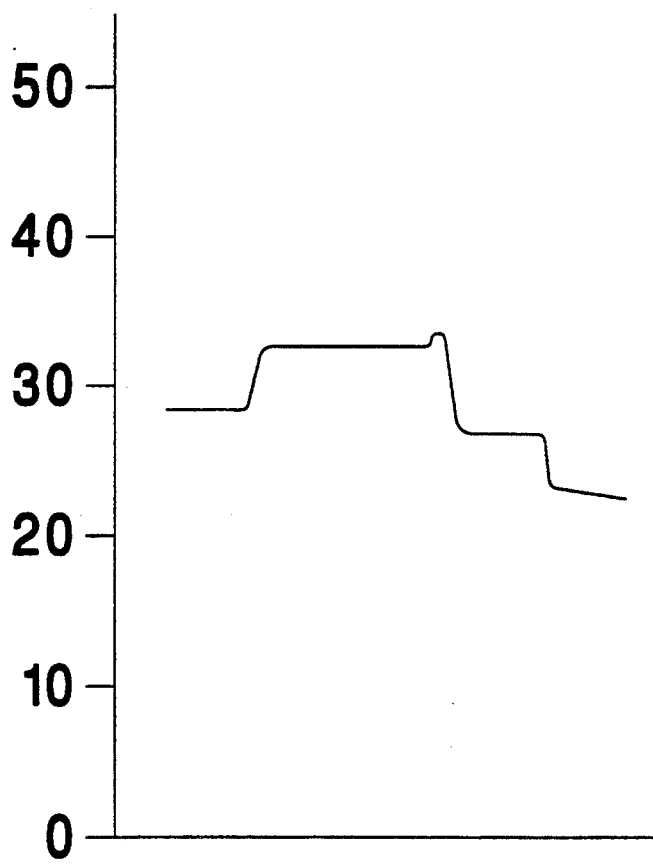
Figure 7A:
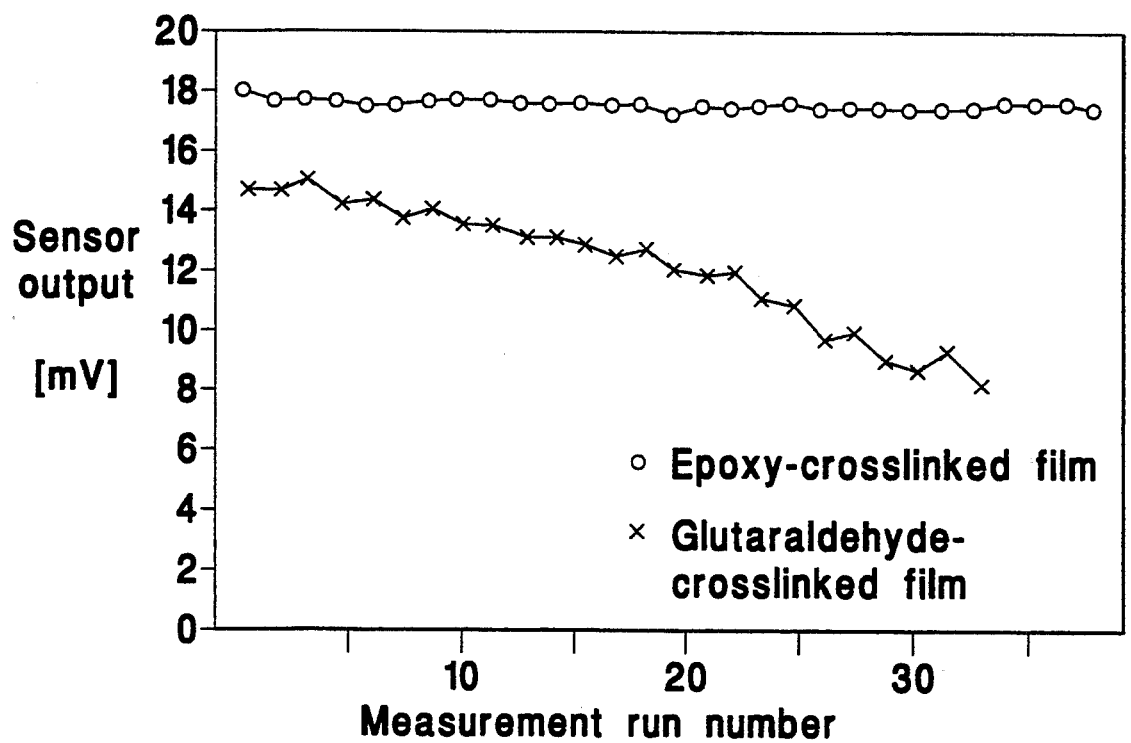
FIGS. 7(a) and 7(b) show graphs illustrating changes in the sensor outputs of urea sensors employing an epoxy crosslinked film and a glutaraldehyde crosslinked film, respectively, depending on the number of runs of measurement continuously made.

The thickness of the thus formed film was measured by the Talystep method. As shown in FIG. 6(b), the film had a uniform thickness with no fins at the both ends thereof. FIG. 6(a) shows the thickness of the conventional glutaraldehyde-crosslinked film. When these films were employed in urea sensors using urease as the enzyme to observe the enzyme activity thereof in the process of forming immobilized enzyme films, while the enzyme activity of the conventional glutaraldehyde-crosslinked film dropped to about 10%, the immobilized enzyme film formed employing a crosslinking agent having at least two epoxy groups in the molecule according to the present invention showed 90% retention of its enzyme activity. Further, the reduction of enzyme activity during continuous use of the sensor can be prevented, as shown in FIG. 7(a), providing a sensor which suffers no significant enzyme deactivation (shown by ○ in FIG. 7) compared with that in the conventional glutaraldehyde-crosslinked film (shown by X in FIG. 7).

EXAMPLE 4

Figure 7B:
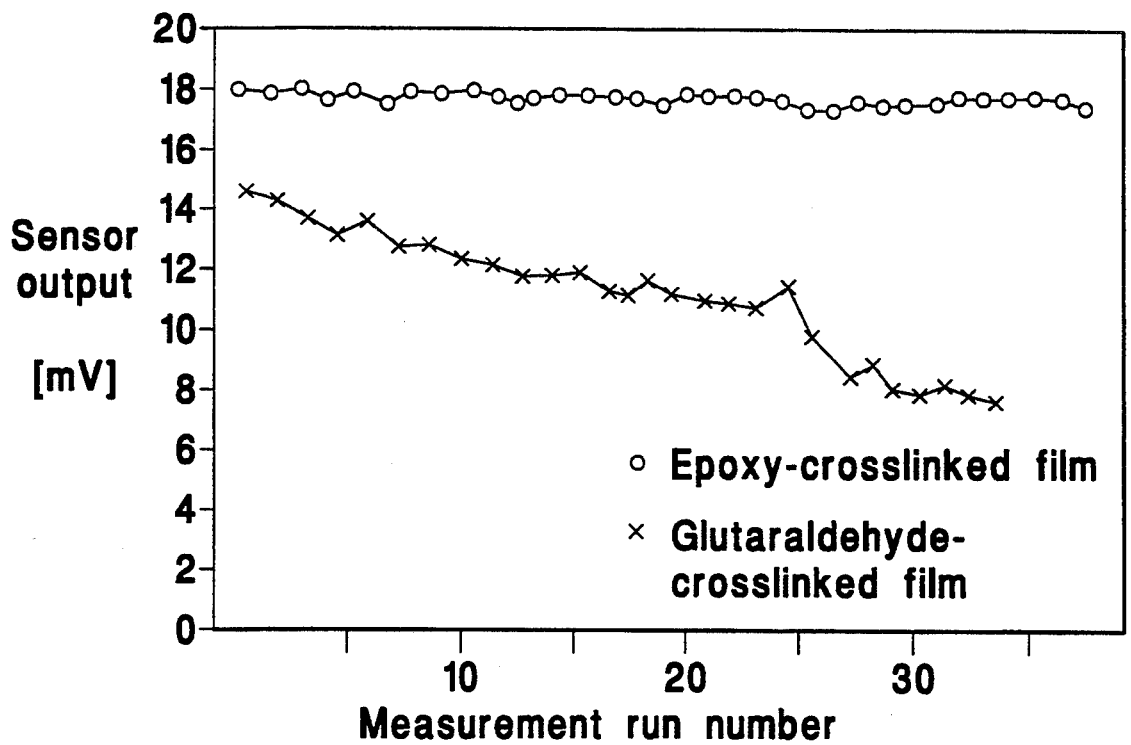

An immobilized enzyme film was formed in the same manner as in Example 3, except that the step of applying the silane coupling agent by spin coating was followed by the step of applying a 100 wt % water-soluble crosslinking agent 28 having at least two epoxy groups in the molecule (see FIG. 5(e)). As shown in FIG. 6(b), the thus formed film had a uniform thickness with no fins on both ends. When this film was employed in a urea sensor using urease as the enzyme to observe the enzyme activity thereof, while the enzyme activity of the conventional glutaraldehyde-crosslinked film dropped to about 10%, the immobilized enzyme film formed employing the crosslinking agent having at least two epoxy groups in the molecule according to the present invention showed 90% retention of its enzyme activity. Further, the reduction of enzyme activity during continuous use of the sensor can be prevented, as shown in FIG. 7(b), providing a sensor which suffers no significant enzyme deactivation (shown by ○ in FIG. 7) compared with that in the conventional glutaraldehyde-crosslinked film (shown by X in FIG. 7). In addition, the number of the sensors in which the films were peeled during use was 4/10 in the group treated with the silane coupling agent only (Example 3) and 0/10 in the group further treated with a water-soluble crosslinking agent having at least two epoxy groups in the molecule (Example 4), exhibiting further enhanced adhesion between the film and the wafer.

EXAMPLE 5

As shown in cross-sectional views in the flow diagram of FIGS. 5(a) to 5(d), an organic solvent-soluble photoresist 21 was applied onto a semiconductor wafer having formed thereon an ISFET (see FIG. 5(a)), followed by a step of removing the photoresist at a predetermined portion on the surface of the ISFET where a protein immobilized film was to be formed by photolithography (see FIG. 5(b)), a step of applying by spin coating a silane coupling agent to treat the predetermined portion on the surface of the ISFET with the silane coupling agent, a step of applying by spin coating a mixture prepared by adding 1 part by weight of a 100 wt % water-soluble crosslinking agent having at least two epoxy groups in the molecule to 2 parts by weight of a 30 wt % aqueous albumin solution, and then adding 1 part by weight of 2 wt % glutaraldehyde thereto to form a protein immobilized film 28 (see FIG. 5(c)), and a step of treating the thus treated semiconductor wafer with an organic solvent in which the photoresist is soluble to dissolve the photoresist and lift off the protein immobilized film present at the portions other than the predetermined portion on the surface of the ISFET (see FIG. 5(d)); wherein the spin coating of the aqueous albumin solution containing a crosslinking agent was repeated at predetermined intervals necessary for the crosslinking agent to complete the crosslinking reaction, whereby to form a protein immobilized film having a desired thickness at the predetermined portion on the surface of the ISFET. When the thickness of the thus formed film was measured by the Talystep method, the film was found to have a uniform thickness with no fins at the both ends thereof.

EXAMPLE 6

A protein immobilized film was formed in the same manner as in Example 5, except that the step of applying the silane coupling agent by spin coating was followed by a step of applying a 100 wt % water-soluble crosslinking agent containing at least two epoxy groups in the molecule (see FIG. 5(e)). When the thickness of the thus formed film was measured by the Talystep method, the film was found to have a uniform thickness with no fins at the both ends thereof. Moreover, the film exhibited further enhanced adhesion with the wafer.

Incidentally, if the concentration of the enzyme-containing aqueous protein solution, water-soluble crosslinking agent or glutaraldehyde is not within the range as set forth in the appended Claims, it will be difficult to maintain the activity of the film and to form a film having an appropriate gelatinous state.

As has been described heretofore, the greatest feature of the present invention resides in the use of the water-soluble crosslinking agent having at least two epoxy groups in the molecule for crosslinking the protein immobilized film or the immobilized enzyme film, whereby the film is made hydrophilic, and thus can be protected from drying and allowed to have elasticity so as to prevent deactivation of the enzyme, giving stable measurement responses when it is employed in semiconductor biosensors.

Meanwhile, the protein immobilized film or the immobilized enzyme film formed according to the process of the present invention has a uniform thickness with no fins on both ends and can exhibit a higher enzyme activity than in the conventional films crosslinked with glutaraldehyde.

What is claimed is:

1. An immobilized enzyme film, characterized in that said film is formed using an enzyme solution prepared by adding 1 to 3 parts by weight of a 50 to 100 wt % water-soluble crosslinking agent having at least two epoxy groups in the molecule wherein said water-soluble crosslinking agent is ethylene polyethylene glycol diglycidyl ether and 1 to 3 parts by weight of a 1 to 2 wt % glutaraldehyde to 1 to 3 parts by weight of a 10 to 50 wt % aqueous protein solution containing an enzyme.

2. A process for forming an immobilized enzyme film, which comprises:

a step of mixing 1 to 3 parts by weight of a 10 to 50 wt % aqueous protein solution containing an enzyme with 1 to 3 parts by weight of a 50 to 100 wt % water-soluble crosslinking agent having at least two epoxy groups in the molecule wherein said water-soluble crosslinking agent is ethylene polyethylene glycol diglycidyl ether followed by vigorous stirring of the resulting mixture with ice cooling;

a step of adding 1 to 3 parts by weight of a 1 to 2 wt % glutaraldehyde to the resulting mixture with continuous ice cooling, followed by vigorous stirring; and a step of applying the resulting mixture by spin coating to a wafer treated with a silane coupling agent.

3. A process for forming an immobilized enzyme film, which comprises:

(a) a step of applying a photoresist soluble in an organic solvent onto a semiconductor wafer on which an ion-sensitive field effect transistor has been formed, followed by removal of the photoresist at a predetermined portion on the surface of the ion-sensitive field effect transistor where an immobilized enzyme film is to be formed;

(b) a step of applying a silane coupling agent by spin coating to treat the predetermined portion on the surface of the ion-sensitive field effect transistor with the silane coupling agent;

(c) a step of applying an aqueous protein solution containing an enzyme and a crosslinking agent onto the thus treated surface of the semiconductor wafer by spin coating; and (d) a step of treating the resulting semiconductor wafer with an organic solvent in which the photoresist is soluble to dissolve the photoresist and lift off the immobilized enzyme film present on the portions other than the predetermined portion on the surface of the ion-sensitive field effect transistor;

wherein the above spin coating step is repeated at predetermined intervals necessary for the crosslinking agent to complete the crosslinking reaction, whereby to form an immobilized enzyme film having a desired thickness at the predetermined portion on the surface of the ion-sensitive field effect transistor; the aqueous protein solution containing an enzyme and a crosslinking agent consisting at least of 1 to 4 parts by weight of a solution containing 1 to 20 % by weight of an enzyme and 10 to 50 % by weight of a protein, 1 to 2 parts by weight of a solution containing 50 to 100 % by weight of a water-soluble crosslinking agent having at least two epoxy groups in the molecule wherein said water-soluble crosslinking agent is ethylene polyethylene glycol diglycidyl ether and 1 to 2 parts by weight of a solution containing 1 to 2 % by weight of glutaraldehyde.

4. The process for forming an immobilized enzyme film according to claim 3, wherein the step of treating the predetermined portion on the surface of the ion-sensitive field effect transistor with a silane coupling agent is followed by a step of applying a water-soluble crosslinking agent having at least two epoxy groups in the molecule wherein said water-soluble crosslinking agent is ethylene polyethylene glycol diglycidyl ether onto the surface of the semiconductor wafer by spin coating.

5. The process for forming an immobilized enzyme film or a protein immobilized film according to claim 3, wherein said silane coupling agent is triethoxyvinylsilane, ethoxydimethylvinylsilane, allyltriethoxysilane or 3-aminopropylethoxysilane.

6. A process for forming a protein immobilized film, which comprises:

(a) a step of applying a photoresist soluble in an organic solvent onto a semiconductor wafer on which an ion-sensitive field effect transistor has been formed, followed by removal of the photoresist at a predetermined portion on the surface of the ion-sensitive field effect transistor where a protein immobilized film is to be formed;

(b) a step of applying a silane coupling agent by spin coating to treat the predetermined portion on the surface of the ion-sensitive field effect transistor with the silane coupling agent;

(c) a step of applying an aqueous protein solution containing a crosslinking agent onto the thus treated surface of the semiconductor wafer by spin coating; and (d) a step of treating the resulting semiconductor wafer with an organic solvent in which the photoresist is soluble to dissolve the photoresist and lift off the protein immobilized film present on the portions other than the predetermined portion on the surface of the ion-sensitive field effect transistor;

wherein the above spin coating step is repeated at predetermined intervals necessary for the crosslinking agent to complete the crosslinking reaction, whereby to form a protein immobilized film having a desired thickness at the predetermined portion on the surface of the ion-sensitive field effect transistor; the aqueous protein solution containing an enzyme and a crosslinking agent being a solution consisting at least of 1 to 4 parts by weight of a solution containing 10 to 50 % by weight of an aqueous protein solution, 1 to 2 parts by weight of a solution containing 50 to 100 % by weight of a water-soluble crosslinking agent having at least two epoxy groups in the molecule wherein said water-soluble crosslinking agent is ethylene polyethylene glycol diglycidyl ether and 1 to 2 parts by weight of a solution containing 1 to 2 % by weight of glutaraldehyde.

7. The process for forming a protein immobilized film according to claim 6, wherein the step of treating the predetermined portion on the surface of the ion-sensitive field effect transistor with a silane coupling agent is followed by a step of applying a water-soluble crosslinking agent having at least two epoxy groups in the molecule wherein said water-soluble crosslinking agent is ethylene polyethylene glycol diglycidyl ether onto the surface of the semiconductor wafer by spin coating.

8. The process for forming an immobilized enzyme film or a protein immobilized film according to claim 6, wherein said silane coupling agent is triethoxyvinylsilane, ethoxydimethylvinylsilane, allyltriethoxysilane or 3-aminopropylethoxysilane.

9. The immobilized enzyme film of claim 1 wherein the enzyme is a urease.

10. The process of claim 2 wherein the enzyme is a urease.

11. The process of claim 3 wherein the enzyme is a urease.

* * * * *